US007547818B2

(12) United States Patent
Stice

(10) Patent No.: US 7,547,818 B2
(45) Date of Patent: Jun. 16, 2009

(54) METAPHASE DONOR CELLS FOR EFFECTIVE NUCLEAR REPROGRAMMING IN MAMMALS

(75) Inventor: Steven Stice, Athens, GA (US)

(73) Assignee: The University of Georgia research Foundation, Inc., Athens, GA (US)

( * ) Notice: Subject to any disclaimer, the term of this patent is extended or adjusted under 35 U.S.C. 154(b) by 547 days.

(21) Appl. No.: 10/809,738

(22) Filed: Mar. 25, 2004

(65) Prior Publication Data

US 2004/0187173 A1  Sep. 23, 2004

Related U.S. Application Data

(62) Division of application No. 09/809,662, filed on Mar. 15, 2001, now Pat. No. 6,906,238.

(60) Provisional application No. 60/189,686, filed on Mar. 15, 2000.

(51) Int. Cl.
*C12N 15/00* (2006.01)
(52) U.S. Cl. .......................... 800/24; 435/373
(58) Field of Classification Search .................. 800/24; 435/377
See application file for complete search history.

(56) References Cited

U.S. PATENT DOCUMENTS

| 4,994,384 | A | 2/1991 | Prather et al. |
| 5,057,420 | A | 10/1991 | Massey |
| 5,096,822 | A | 3/1992 | Rosenkrans, Jr. et al. |
| 5,160,312 | A | 11/1992 | Voelkel |
| 5,213,979 | A | 5/1993 | First et al. |
| 5,366,888 | A | 11/1994 | Fry et al. |
| 5,453,366 | A | 9/1995 | Sims et al. |
| 5,480,772 | A | 1/1996 | Wangh |
| 5,496,720 | A | 3/1996 | Susko-Parrish et al. |
| 5,651,992 | A | 7/1997 | Wangh |
| 5,773,217 | A | 6/1998 | Wangh |
| 5,945,577 | A | 8/1999 | Stice et al. |
| 6,235,969 | B1 | 5/2001 | Stice et al. |

FOREIGN PATENT DOCUMENTS

| EP | 0 521674 A1 | 1/1993 |
| GB | GP 2 340 943 A | 2/2000 |
| WO | WO 90/13627 | 11/1990 |
| WO | WO 95/16770 | 6/1995 |
| WO | WO 96/07732 | 3/1996 |
| WO | WO 97-07668 | 3/1997 |
| WO | WO 97-07669 | 3/1997 |
| WO | WO 98/07841 | 2/1998 |
| WO | WO 98/39416 | 9/1998 |

OTHER PUBLICATIONS

Simerly, C. et al. Molecular Correlates of Primate Nuclear Transfer Failures. Science. Apr. 11, 2003, vol. 300, p. 297.*

Mitalipov et al. Rhesus Monkey Embryos Produced by Nuclear Transfer from Embryonic Blastomeres or Somatic Cells. Biology of Reproduction. 2002, vol. 66, pp. 1367-1373.*
Campell et al. Improved Development to Blastocyst of Ovine Nuclear Transfer Embryos Reconstructed during the Presumptive S-Phase of Enucleated Activated Oocytes. Biology of Reproduction. 1994, vol. 50, 1385-1393.*
Campbell. Nuclear Transfer in Farm Animal Species. Cell & Develop. Bilol. 1999, vol. 10, pp. 245-252.*
Abeydeera et al. "Glutathione content and embryo development after in vitro fertilisation of pig oocytes matured in the presence of a thiol compound and various concentrations of cysteine," *Zygote*. Aug. 1999; 7(3):203-10.
Abeydeera et al., "Development and viability of pig oocytes matured in a protein-free medium containing epidermal growth factor," *Theriogenology*. Sep. 15, 2000; 54(5):787-97.
Alessi et a., "The cyclin-dependent kinase inhibitors olomoucine and roscovitine arrest human fibroblasts in G1 phase by specific inhibition of CDK2 kinase activity," *Exp Cel Res*. Nov. 25, 1998; 245(1):8-18.
Baguisi et al., "Induced encleation in nuclear transfer procedures to produce cloned animals," *Theriogenology*. Jan. 1, 2000; 53(1):209.
Barnes et al., "Influence of recipient oocyte cell cycle stage on DNA synthesis, nuclear envelope breakdown, chromosome constitution, and development in nuclear transplant bovine embryos," *Mol Reprod Dev*. Sep. 1993; 36(1):33-41.
Betthauser et al., "Production of cloned pigs from in vitro systems," *Nat Biotechnol*. Oct. 2000; 18(10):1055-9.
Campbell et al., "Sheep cloned by nuclear transfer from a cultured cell line," *Nature*. Mar. 7, 1996; 380(6569):64-6.
Chastant-Maillard et al., "Clonage et Reprogrammation du Noyau dans l'embryon Préimplantatoire," *Gynécol Obstét Ferril*, (2000), vol. 28, pp. 649-658.
Cheong et al., "Birth of mice after transplantation of early cell-cycle-stage embryonic nuclei into enucleated oocytes," *Biol Reprod*. May 1993; 48(5):958-63.
Cibelli et al., "Cloned transgenic calves produced from nonquiescent fetal fibroblasts," *Science*. May 22, 1998; 280(5367):1256-8.
Collas et al., "Nuclear transplantation by microinjection of inner cell mass and granulosa cell nuclei," *Mol Reprod Dev*. Jul. 1994; 38(3):264-7.
Collas et al. (1992) Influence of Cell Cycle Stage of the Donor Nuclear on Development for Nuclear Transplant Rabbit Embryos. Biology of Reproduction. vol. 46, pp. 492-500.
Compton, "New tools for the antimitotic toolbox," *Science*. Oct. 29, 1999; 286(5441):913-4.

(Continued)

*Primary Examiner*—Deborah Crouch
(74) *Attorney, Agent, or Firm*—Clark G. Sullivan; Arnall Golden Gregory LLP

(57) ABSTRACT

The present invention provides methods of producing a clone non-human mammalian nuclear transfer (NT) embryo and methods for producing a cloned non-human mammal. Embodiments of the methods include introducing doner genetic material into a metaphase I oocyte; introducing donor genetic material into a non-enucleated oocyte; introducing donor genetic material obtained from a donor cell that is a metaphase into an oocyte; introducing donor genetic material into an oocyte, and naturally activating the oocyte or the NT embryo; and introducing donor genetic material obtained from a donor cell that is at late G1 phase into anoocyte.

4 Claims, No Drawings

OTHER PUBLICATIONS

Compton, "An improved Method for Routine Preparation of Intact Artificial Chromosome DNA (340-1000 kb) for Transfection into Human Cells" *Nucleic Acids Res.* 1999, vol. 27, No. 7, pp. 1762-1765.

Curnock et al., "Embryo transfer in pigs: a method for introducing genetic material into primary specific-pathogen-free herds," *Am J Vet Res.* Jan. 1976; 37(1):97-8.

De Sutter et al., "Parthenogenetic activation of human oocytes by puromycin," *J Assist Reprod Genet.* Aug. 1992; 9(4):328-37.

De Vos et al., "In-vitro matured metaphase-I oocytes hava a lower fertilization rate but similar embryo quality as mature metaphase-II oocytes after intracytoplasmic sperm injection," *Hum Reprod.* Jul. 1999; 14(7):1859-63.

Du et al., "Development of nuclear transfer embryos using porcine fetal fibroblasts," *Theriogenology,* Jan. 1, 1999; 51(1):201.

Fehilly et al. (1985) Cytogeentic and Blood Group Studies of Sheep/Goat Chimaeras. *J. Reprod. Fert.* 1985., vol. 74, pp. 215-221.

Gandhi et al., "Substrate utilization in porcine embryos cultured in NCSU23 and G1.2/G2.2 sequential culture media," *Mol Reprod Dev.* Mar. 2001; 58(3):269-75.

Gibbons, John R., "Novel Pig Cloning Procedures for Xenotransplantation," Grant Abstract, Grant No. 1R43HL065806-01 [online]. National Heart, Lung, and Blood Institute, National Institutes of Health, project dates Sep. 1, 2000-Feb. 28, 2001 [retrieved on Sep. 24, 2001]. Retrieved from the Internet: URL: <http://commons.cit.nih.gov/crisp3/crisp_lib.getdoc?textkey=6211180&p_grant_num=1R43HL065806-01&p_query=&ticket=89400&p_audit_session_id=1131851&p_keywords=>, 2 pages.

Goto et al., "Birth of cloned calves derived from cultured oviductal epithelial cells of a dairy cow," *Anim Sci J.* 1999; 70(4):243-245.

Graham, "The fusion of cells with one- and two-cell mouse embryos," *Wistar Inst Symp Monogr.* 1969; 9:19-35.

Gulyas, "Ultrastructural observations on rabbit, hamster and mouse eggs following electrical stimulation in vitro," *Am J Anat.* Oct. 1976; 147(2):203-18.

Hazeleger et al., "State of the art in pig embryo transfer," *Theriogenology.* Jan. 1, 1999; 51(1):81-90.

Hill, et al., "Clinical and pathologic features of cloned transgenic calves and fetuses (13 case studies)," *Theriogenology.* Jun. 1999; 51(8):1451-65.

Inoue et al., "Activation of mitogen-activated protein kinase during meiotic maturation in porcine oocytes," *Zygote.* Aug. 1995; 3(3):265-71.

Kato et al., "Eight calves cloned from somatic cells of a single adult," *Science.* Dec. 11, 1998; 282(5396):2095-8.

Keefer et al., "Effect of Follicle-Stimulating Hormone an Luteinizing Hormone During Bovine In Vitro Maturation on Development Following In Vitro Fertilization and Nuclear Transfer," *Molecular Reproduction and Development,* (1993), vol. 36, pp. 469-474.

Kikuchi et al., "Cytoplasmic maturation for activation of pig follicular oocytes cultured and arrested a metaphase I," *J Reprod Fertil. I* May 1999; 116(1):143-56.

Kikyo et al., "Reprogramming Nuclei: Insights From Cloning, Nuclear Transfer and Heterokaryons," *Journal of Cell Science,* (2000), vol. 113, pp. 11-20.

Kubota et al., "Six cloned calves produced from adult fibroblast cells after long-term culture," *Proc Natl Acad Sci U S A.* Feb. 1, 2000; 97(3):990-5.

Kühholzer et al., "Production of transgenic porcine blastocytes by nuclear transfer," *Mol Reprod Dev.* Jun. 2000; 56(2):145-8.

Kwon et al., "Production of identical sextuplet mice by transferring metaphase nuclei from four-cell embryos," *Proc Natl Acad Sci U S A.* Nov. 12, 1996; 93(23):13010-3.

Liu et al., "Parthenogenetic development and protein patterns of newly matured bovine oocytes after chemical activation," *Mol Reprod Dev.* Mar. 1998; 49(3):298-307.

Machaty et al., "Complete activation of porcine oocytes induced by the sulfhydryl reagent, thimerosal," *Biol Reprod.* Nov. 1997; 57(5):1123-7.

Meirelles et al Complete Replacement of the Mitochondrial Genotype in a Bos indicus calf Reconstituted by Nuclear Transfer to a Bos Taurus Oocyte. Genetics. May 2001, vol. 158, pp. 351-356.

Miyoshi et al., "Improvement in development of porcine embryos reconstituted with cells from blastocyst-derived cell lines and enucleated oocytes by optimization of reconstruction methods." *Cloning.* 2000; 2(4):175-184.

Miyoshi et al., "Establishment of a porcine cell line from in vitro-produced blastocysts and transfer of the cells into enucleated oocytes," *Biol Reprod.* Jun. 2000; 62(6):1640-6.

Miyoshi et al., "Development of Porcine Embryos Reconstituted with Somatic Cells and Enucleated Metaphase I and II Oocytes Matured in a Protein-free Medium," *BMC Developmental Biology,* (2001), vol. 1.

Miyoshi et al., "Transfer of porcine blastocyst-derived cells into enucleated oocytes," *Theriogenology.* Jan. 1, 2001; 51(1):201.

Ogura et al., "Development of normal mice from metaphase I oocytes fertilized with primary spermatocytes," *Proc Natl Acad Sci U S A.* May 12, 1998; 95(10):5611-5.

Onishi et al., "Pig cloning by microinjection of fetal fibroblast nuclei," *Science.* Aug. 18, 2000; 289(5482):1188-90.

Ono et al., "Cloned mice from fetal fibroblast cells arrested at metaphase by a serial nuclear transfer," *Biol Reprod.* Jan. 2001; 64(1):44-50.

Polejaeva et al., "Cloned pigs produced by nuclear transfer from adult somatic cells," *Nature.* Sep. 7, 2000:407(6800):86-90.

Polejaeva et al., "New Advances in Somatic Cell Nuclear Transfer: Application in Transgenesis," *Theriogenology.* (2000), vol. 52, No. 1, pp. 117-126.

Powell et al., "Effects of fibroblast source and tissue-culture medium on success of bovine nuclear transfer with transfected cells," *Theriogenology.* Jan. 1, 2001; 51(1):287.

Prather et al., "Nuclear transplantation in the bovine embryo: Assessment of donor nuclei and recipient oocyte." *Biol Reprod.* Nov. 1987; 37(4):859-66.

Prather et al., "Nuclear transplantation in early pig embryos," *Biol Reprod.* Sep. 1989; 41(3):414-8.

Prather et al., "Development of the techniques for nuclear transfer in pigs," *Theriogenology.* Jan. 15, 1999; 51(2):487-98.

Seshagiri et al., "Glucose inhibits development of hamster 8-cell embryos in vitro," *Biol Reprod.* Mar. 1989; 40(3):599-606.

Stice et al., "Nuclear reprogramming in nuclear transplant rabbit embryos," *Biol Reprod.* Oct. 1988; 39(3):657-64.

Stice et al., "Bovine nuclear transfer embryos: oocyte activation prior to blastomere fusion," *Mol Reprod Dev.* May 1994; 38(1):61-8.

Stice et al., "Cloning: New Breakthroughs Leading to Commercial Opportunities," *Theriogenology,* (1998), vol. 49, pp. 129-138.

Stice et al., "Pluripotent bovine embryonic cell lines direct embryonic development following nuclear transfer," *Biol Reprod.* Jan. 1996; 54(1):100-10.

Susko-Parrish et al., "Inhibition of protein kinases after an induced calcium transient causes transition of bovine oocytes to embryonic cycles without meiotic completion," *Dev Biol.* Dec. 1994; 166(2):729-39.

Szöllösi et al., "Inhibition of protein kinases by 6-dimethylaminopurine accelerates the transition to interphase in activated mouse oocytes," *J Cell Sci.* Mar. 1993; 104(Pt 3):861-72.

Tani et al., "Direct exposure of chromosomes to nonactivted ovum cytoplasm is effective for bovine somatic cell nucleus reprogramming," *Biol Reprod.* Jan. 2001; 64(1):324-30.

Tao et al., "Development of pig embryos by nuclear transfer of cultured fibroblast cells," *Cloning.* 1999; 1(1):55-62.

Tao et al., "Development of pig embryos reconstructed by microinjection of cultured fetal fibroblast cells into in vitro matured oocytes," *Anim Reprod. Sci.* Jun. 28, 1999:56(2):133-41.

Tervit et al., "Successful culture in vitro of sheep and cattle ova," *J Reprod Fertil.* Sep. 1972; 30(3):493-7.

Wakayama et al., "Full-term development of mice from enucleated oocytes injected with cumulus cell nuclei," *Nature.* Jul. 23, 1998; 394(6691):369-74.

Wakayama et al., "Mice cloned from embryonic stem cells," *Proc Natl Acad Sci U S A.* Dec. 21, 1999; 96(26):14984-9.

Wells et al., "Production of cloned calves following nuclear transfer with cultured adult mural granulosa cells," *Biol Reprod.* Apr. 1999; 60(4):996-1005.

Wickramasinghe et al., "Centrosome phosphorylation and the developmental expression of meiotic competence in mouse oocytes," *Dev Biol.* Jul. 1992; 152(1):62-74.

Willadsen, "Nuclear transplantation in sheep embryos," *Nature.* Mar. 6, 1986; 320(6057):63-5.

Wilmut et al., "Viable offspring derived from fetal and adult mammalian cells," *Nature.* Feb. 27, 1997; 385(6619):810-3.

Yang et al., Electric field-induced activation of rabbit oocytes, *Biol Reprod.* Jul. 1992; 42 (Suppl 1):117(abstract 268).

Yang et al., "Nuclear Totipotency of Cultured Rabbit Morulae to Support Full-term Development Following Nuclear Transfer" *Biology of Reproduction.* 1992; vol. 47, 636-643.

Zimmerman et al., "Electric field-induced cell-to-cell fusion," *J Membr Biol.* 1982; 67(3):165-82.

\* cited by examiner

METAPHASE DONOR CELLS FOR EFFECTIVE NUCLEAR REPROGRAMMING IN MAMMALS

CONTINUING APPLICATION DATA

This application is a Divisional of U.S. patent application Ser. No. 09/809,662, filed Mar. 15, 2001 now U.S. Pat. No. 6,906,238, and claims the benefit of U.S. Provisional Patent Application No. 60/189,686, filed Mar. 15, 2000, both of which are incorporated herein by reference.

GOVERNMENT FUNDING

The present invention was made with government support under Grant No. 1 R43 HL65806-01, awarded by Dept of Health and Human Services. The Government has certain rights in this invention.

BACKGROUND

Mammalian nuclear transfer procedures were developed in the late 1980s. The basic nuclear transfer procedure includes the enucleation of an oocyte in metaphase II (MII), and the transfer of a donor nucleus by fusion or injection into the enucleated oocyte. An important aspect of nuclear transfer is the reprogramming of the donor nucleus. Nuclear reprogramming refers to modifying a nucleus so the nucleus is capable of directing development from the one-cell embryo stage to offspring.

The first cloned rabbit was produced using embryonic cells as a source of donor nuclei. Over the last decade, the source of the donor has been expanded to include differentiated cells as well (Table 1). For example, the first cloned transgenic calves were produced recently using donor nuclei from fetal cells. Both studies used unfertilized MII oocytes that were first enucleated and then fused with the donor cell.

TABLE 1

Species and donor cell type used to produce cloned mammals.

Cell type used to produce a nuclear transfer offspring (clones)

| Species | Embryonic | Fetal | Adult |
|---|---|---|---|
| Mouse | Cheong et al., 1994 | None reported | Wakayama et al., 1998 |
| Rabbit | Stice and Robl, 1988 | None reported | None reported |
| Cattle | Prather et al., 1987 | Cibelli et al., 1998 | Kato et al., 1998 |
| Sheep | Willadsen, 1986 | Campbell et al., 1996 | Wilmut et al., 1997 |
| Pig | Prather et al., 1989 | Onishi et al., 2000 | Polejaeva et al., 2000 |

Citations: Campbell et al., Nature, 380, 64 (1996); Cheong et al., Biol. Reprod., 48, 958 (1993); Cibelli et al., Science, 280, 1256 (1998); Kato et al., Science, 282, 2095 (1998); Onishi et al., Science, 289, 1188 (2000); Prather et al., Biol. Reprod., 37, 859 (1987); Polejaeva et al., Nature, 407, 86 (2000); Prather et al., Biol. Reprod..., 41, 414 (1989); Stice et al., Biol. Reprod., 39, 657(1988); Wakayama et al., Nature, 394, 369 (1998); Willadsen et al., Nature, 320, 63 (1986); and Wilmut et al., Nature, 385, 810 (1997).

Successful cloning using undifferentiated embryonic cells versus differentiated cells as a source of donor nuclei for introduction to an MII oocyte may depend on the order in which fusion and activation are performed. Bovine embryonic cell-derived clones developed at a higher rate when the MII oocyte was activated first followed by introduction of the donor nucleus into the activated oocyte (Barnes et al., Mol. Reprod. Dev., 36, 33 (1993); Stice et al., Mol. Reprod. Dev., 38, 61 (1994)). Bovine fetal and adult cell cloning was accomplished by reversing the fusion and activation steps in the cloning process, and resulted in the first cloned cattle fetuses from differentiated cell lines, and later in offspring from fetal cells (Cibelli et al., Science, 280, 1256 (1998); Stice et al., Biol. Reprod., 54, 100 (1996)).

In addition, the state of the donor cell used for cloning has varied. Dolly was the result of using donor cells that were quiescent (Wilmut et al., Nature, 385, 810 (1997)). However, other studies using quiescent cells have produced very different results. Various mouse cells that are naturally in a quiescent state (cumulus cells, sertoli cells and neural cells) were harvested and used in cloning procedures. The cumulus cells gave rise to offspring while the other quiescent cells did not. Arguably, the least quiescent of the three cell types is the cumulus cells since these are often mixed with granulosa cells which will propagate very well in culture. Cibelli and coworkers (Science, 280, 1256 (1998); Stice et al., (U.S. Pat. No. 5,945,577)) demonstrated that non-serum starved proliferating bovine fetal fibroblast cells were a suitable donor source for nuclear transfer with efficiencies similar to reports using serum-starved (i.e., quiescent) cells. In addition, adult mouse fibroblast cells cultured in serum and no serum were compared but both groups resulted in low developmental rates to term. To date no firm conclusion can be made on whether quiescent or proliferating cells are the best sources of donor cells for nuclear transfer. Neither methods using quiescent cells nor proliferating cells appear to result in marked improved cloning efficiencies or outcomes.

Improvements in oocyte activation in various species have been vigorously pursued (reviewed in Prather et al., Theriogen., 51, 498 (1999)). Progress has been made by increasing calcium and/or decreasing protein phosphorylation in the oocyte (mice, Szollosi et al., J. Cell Sci., 104, 861 (1994); cattle, Susko-Parrish et al., Dev. Biol., 166, 729 (1994) and Susko-Parrish et al., (U.S. Pat. No. 5,496,720)).

Cloning pigs in particular is technically difficult. A cloned pig derived from four-cell stage embryo nucleus was reported in 1989 (Prather et al., Biol. Reprod., 41, 414-8 (1989)). Some groups have produced blastocyst stage pig nuclear transfer embryos derived from differentiated cells (Table 2).

TABLE 2

Procine fetal fibroblast cells (G0/G1) fused into enucleated MII oocytes and development of resulting nuclear transfer (NT) embryos.

| Reference | Number of NT embryos produced | Number of NT embryos developing to morula and blastocyst stage (%) | Number of offspring |
|---|---|---|---|
| Du et al., 1999 | 81 | 5 (8) | Quality too poor to transfer |
| Miyoshi et al., 1999 | 36 | 1 (3) | Quality too poor to transfer |
| Tao et al., 1999 | 100 | 3 (7) | Average nuclei in blast was 19.5 |

Citations: Du et al., Theriogenology, 51, 201 (1999); Miyoshi et al., Theriogen., 51, 210 (1999); and Tao et al., Cloning, 1, 55 (1999).

Improvements in porcine oocyte activation have lagged behind other species, particularly in development of the activated unfertilized oocyte (i.e., parthenogenetic development). Recently, pig cloning has been reported (Onishi et al., Science, 289, 1188 (August, 2000); Polejaeva et al., Nature, 407, 86 (September, 2000); and Betthauser et al., *Nature Biotechnol.*, 18, 1055 (October, 2000)). However, nuclear transfer embryo developmental rates with in vitro and in vivo derived MII oocytes remain poor. Therefore, there is a need to employ novel changes in the nuclear transfer procedure to produce cloned offspring from differentiated cell types.

SUMMARY OF THE INVENTION

The present invention provides methods for introducing donor genetic material into an oocyte, and for optimizing environmental factors needed for reprogramming donor genetic material that has been introduced into an oocyte. Another advantage of the present invention is that it provides methods for optimizing exposure time of the donor genetic material to the environmental factors needed for reprogramming the donor nucleus.

Accordingly, the present invention provides methods of producing a cloned non-human mammalian nuclear transfer (NT) embryo. In one embodiment, the cloned non-human mammalian NT embryo is produced by introducing donor genetic material into a metaphase I oocyte to yield a cloned non-human mammalian NT embryo. In other embodiments, the cloned non-human mammalian NT embryo is produced by introducing donor genetic material into a non-enucleated oocyte; introducing donor genetic material obtained from a donor cell that is at metaphase into an oocyte; introducing donor genetic material into an oocyte, and naturally activating the oocyte or the NT embryo; or introducing donor genetic material obtained from a donor cell that is at late G1 phase into an oocyte.

The present invention also provides methods for producing a cloned non-human mammal that involve incubating a mammalian NT embryo such that the NT embryo undergoes cell division. In one embodiment, the NT embryo that is incubated to produce the cloned non-human mammal is made by introducing donor genetic material into a metaphase I oocyte. In other embodiments the NT embryo is produced by introducing donor genetic material into a non-enucleated oocyte; introducing donor genetic material obtained from a donor cell that is at metaphase into an oocyte; introducing donor genetic material into an oocyte, wherein the oocyte of the NT embryo is naturally activated; or introducing donor genetic material obtained from a donor cell that is at metaphase into an oocyte.

DETAILED DESCRIPTION OF PREFERRED EMBODIMENTS OF THE INVENTION

The present invention provides methods for cloning non-human mammals. The methods include providing a nuclear transfer (NT) embryo, and optionally transferring it to a host such that the NT embryo undergoes cell division and preferably develops into a fetus or offspring. The NT embryo may be produced by introducing donor genetic material into an oocyte of the same species to result in an NT embryo. The NT embryo may be activated. Activation may occur before or after introducing the donor genetic material to the oocyte, or at about the same time the donor genetic material is introduced to the oocyte. In general, the NT embryo may be transferred into a recipient animal before or after cell division occurs in the NT embryo. Typically, if the NT embryo is transferred after cell division, it is cultured in vitro before the transfer.

Unless otherwise specified herein, the term "oocyte" refers to an unfertilized egg in its natural nucleated state or its enucleated state (i.e., the genetic material that is typically present in the nucleus has been removed). The genetic material typically present in the oocyte nucleus is also referred to herein as maternal genetic material. Maternal genetic material does not include mitochondrial DNA. Unless otherwise specified herein, the term "oocyte" includes oocytes that are either activated or not activated. "Donor genetic material" is the genetic material, obtained from a donor cell, that is introduced into an oocyte. Donor genetic material contains the genetic material that is to be cloned and be present in the cloned non-human mammal. An "NT embryo" is the result of introducing donor genetic material into an oocyte, whether the maternal genetic material was removed from the oocyte before transfer (i.e., the oocyte was enucleated) or not. A one cell NT embryo is also referred to as a zygote. In some aspects of the present invention, an "NT unit" is produced as a stage that precedes the NT embryo. An "NT unit" is the result of injecting a donor cell, or a nucleus obtained from a donor cell, into an oocyte, for instance into the perivitelline space (i.e., the space between an oocyte and the zona pellucida). An "NT unit" becomes an NT embryo when the donor cell is fused with the oocyte. An NT embryo may contain the maternal genetic material that was originally present in the oocyte.

Oocytes

Suitable non-human mammalian sources for oocytes include ungulates, e.g., caprine, ovine, bovine, porcine, and equine animals, as well as guinea pigs, mice, hamsters, rats, primates, etc. Preferably, the oocytes are obtained from sheep, cows, or pigs, most preferably cows or pigs. Typically, oocytes are obtained from the ovaries or reproductive tract of a mammal. Slaughterhouse materials provide a readily available source of oocytes. Alternatively, oocytes can be surgically removed and used in the methods of the present invention. Methods for isolation of oocytes are well known in the art. For instance, the collection of immature bovine oocytes is described by Wells et al. (*Biol. Reprod.*, 60, 996-1005 (1999)), and collection of immature porcine oocytes is described by Abeydeera et al. (*Zygote* 7, 203-10 (1999)) and Stice et al., (U.S. Pat. No. 5,945,577). Whole oocytes or bisected oocytes can be used in the present methods. Preferably whole oocytes are used.

A mature oocyte can be in vitro derived or in vivo derived. In vitro derived oocytes are initially collected from an animal, typically by aspiration of ovarian follicles, while the oocytes are immature. An immature oocyte is an oocyte that is in prophase. Typically, immature oocytes are subsequently cultured in media and allowed to mature under in vitro conditions. Media that can be used for the in vitro maturation of oocytes are referred to herein as maturation media or in vitro maturation (IVM) medium. Examples include Tissue Culture Medium-199 (TCM-199), Waymouths, and NCSU-23 (described in Abeydeera et al. (*Zygote* 7, 203-10 (1999). Preferably TCM-199 is used for cows and NCSU-23 or TCM-199 is used for pigs. The in vitro maturation of oocytes is known to the art.

Typically, when used in the methods of the present invention, oocytes are at metaphase I (MI) or metaphase II (MII), i.e., stages of meiosis that are well known to the art. Preferably, pig oocytes are at MI, and cow oocytes are at MII up to and including the first polar body extrusion. MAP-kinase and histone H1 kinase activities are high in MI oocytes through the first polar body extrusion at MII, and decrease as the oocyte ages (see, for instance Inoue et al., *Zygote*, 3, 265-71 (1995)). Without intending to be limiting, it is expected that the use of oocytes in MI through the first polar body extrusion at MII allows exposure of donor genetic material to higher MAP-kinase and histone H1 kinase activity as well as other unknown maternal factors than would occur in an MII oocyte that has aged after the first polar body extrusion at MII. After reaching the appropriate stage of meiosis an oocyte can be enucleated as described herein. Alternatively, the genetic material is not removed from the oocyte, i.e., the oocyte is non-enucleated. Preferably, the oocyte is enucleated.

The maturity of in vitro derived oocytes to MI or MII is typically measured as a function of the time the in vitro derived oocytes are incubated in maturation media. Bovine oocytes generally reach the MI stage after about 8 to about 16 hours incubation, more preferably about 8 to about 14 hours, most preferably about 9 to about 12 hours. Pig oocytes generally reach the MI stage about 25 to about 35 hours incubation, preferably about 27 to about 31 hours. An oocyte can be enucleated during these time periods to result in an enucleated MI oocyte.

Alternatively, oocytes can be treated during the maturation process with one or more agents to arrest the oocytes in MI. Oocytes are typically arrested by exposing the cells to at least one arresting agent. Useful arresting agents include those able to prevent the formation of microtubules and/or disorganize (i.e., breakdown) microtubules that have already formed, and microfilament inhibitors. Non-limiting examples of arresting agents include nocodazole, demicolchin, cytochalasin B, cytochalasin D, colchicine, colcemid, and taxol, preferably nocodazole and cytochalasin B. Preferably, the cell cycle arrest of the oocyte is reversible, i.e., the cell resumes proliferating, karyokenesis, or cytokinesis when the arresting agent(s) is removed, or when the arresting agent(s) is counteracted by addition of a counteracting agent.

When an arresting agent is used, it is added before the time the oocytes typically reach MII, preferably while the oocyte is in MI. In increasing order of preference the arresting agent is added to bovine oocytes after between about 8 hours and about 24 hours incubation in in vitro maturation medium, between about 8 hours and about 18 hours, between about 8 hours and about 16 hours, most preferably between about 8 and 12 hours. The oocytes are treated with the arresting agent for about 5 hours. In increasing order of preference the arresting agent is added to pig oocytes after about 24 hours to about 35 hours incubation in in vitro maturation medium, more preferably after about 30 hours to about 35 hours. The oocytes are treated with the arresting agent for about 5 hours. The concentration of the arresting agent used typically varies depending on the arresting agent used. For instance, nocodazole is typically used at a concentration of about 0.1 microgram per milliliter (µg/ml) to about 10 µg/ml, preferably about 0.3 µg/ml, and cytochalsin B is used at a concentration of about 1 µg/ml to about 100 µg/ml, preferably about 1 µg/ml to about 7.5 µg/ml.

Typically, oocytes undergoing in vitro maturation are fairly synchronous; however, the exposure of a population of oocytes to an arresting agent before reaching MII typically does not result in arrest of all the oocytes in MI. Thus, those cells that are arrested are optionally separated from those that are not arrested. Arrested oocytes typically have an altered morphology that allows arrested oocytes to be identified and separated. For instance, oocytes arrested before MII contain condensed sister chromatids and are further characterized by the absence of the first polar body. Preferably, arrested oocytes contain condensed paired sister chromatids. Thus, whether an oocyte is in MI can be assessed by examining the oocyte with a microscope. It will be appreciated by a person of skill in the art that such an examination can advantageously occur when the donor genetic material is introduced to the oocyte.

Bovine oocytes generally reach the MII stage where the first polar body has been extruded after about 12 to about 24 hours incubation, preferably about 16 to about 18 hours. Pig oocytes generally reach the MII stage after about 20 to about 50 hours incubation, preferably about 30 to about 40 hours. Oocytes typically naturally arrest at MII, and typically stay in MII for about 24 hours. It will be appreciated by a person of skill in the art that the time of maturation is a general guide, but morphology is the guide for each individual oocyte.

In vivo derived oocytes are collected from an animal when the oocytes are mature. A mature oocyte can be at MI or at MII. In vivo derived oocytes can be obtained from non-superovulated or superovulated donors. Donors can be induced to superovulate by methods known to the art. For instance, superovulated pig or cow donors can be obtained by treatment with PMSG (pregnant mare serum gonadotrophin) or FSH (follicle stimulating hormone). Preferably, oocytes are obtained from the donor animal when the donor is shortly (about 12 hours) after the onset of estrus. The period of time after the onset of estrus within which the oocytes can be obtained depends on the type of animal and is known to the art. For instance, if the donor animal is a cow or a pig the oocytes are preferably obtained within about 24 hours or about 48 hours of the onset of estrus, respectively.

Typically, in vivo derived oocytes are stripped of their cumulous cells immediately after collection from the donor animals and used in the methods of the present invention. Methods for removing cumulous cells are known to the art (Tao et al., *Anim. Reprod. Sci.*, 56, 133-41 (1999); Stice et al. (U.S. Pat. No. 5,945,577)). Prior to use, the stage of meiosis of the oocytes is determined using methods known to the art.

Donor Genetic Material

Donor genetic material contains the genetic material that is to be introduced into an oocyte and be present in the cloned non-human mammal. Donor genetic material can be isolated from a donor cell, i.e., the cell in which the genetic material is normally present. For instance, a nucleus or metaphase plate may be isolated from the donor cell and then introduced into an oocyte. A metaphase plate is described in further detail hereinbelow. Alternatively and preferably, the donor genetic material is not isolated from the donor cell before the donor genetic material is introduced into an oocyte, i.e., the donor cell itself is introduced into an oocyte, typically by introducing the donor cell into the perivitelline space of an oocyte and then fusing the donor cell with the oocyte as described hereinbelow. Optionally, donor genetic material includes DNA that is genetically engineered or transgenic.

The donor cells used in the methods of the present invention can be undifferentiated or differentiated cells, preferably differentiated. Differentiated mammalian cells are those cells which are beyond the early embryonic stage. More particularly, the differentiated cells are those from at least beyond the embryonic disc stage (for instance, about day 10 of bovine embryogenesis, or about day 8 of pig embryogenesis). Embryogenic stages from at least beyond the embryonic disc stage are referred to herein as late embryogenic stage. Fetal stage cells are those cells that are at least about day 20 to at least about day 30 of embryogenesis up to the time of birth. Adult stage cells are those present in an animal after birth. The differentiated cells may be derived from ectoderm, mesoderm or endoderm; preferably they are derived from mesoderm or endoderm.

Non-human mammalian cells for use as donor cells may be obtained by methods known to the art. Mammalian cells useful in the present invention include cells of the body, including, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells. The mammalian cells that can be used in the methods of the present invention may be obtained from different organs, e.g., skin, lung, pancreas, liver, stomach, intestine, heart, reproductive organs, bladder, kidney, urethra and other urinary organs. The mammalian cells may be somatic or diploid germ cells obtained from embryo, fetus, or adult tissue, or from cultured cell lines, preferably adult tissue. The use of adult cells is advantageous as it allows the cloning of animals having desirable characteristics. These are just examples of suitable cells that can be used as a source of donor genetic material. Preferably, the cells are fibroblasts or granulosa cells.

In an aspect of the invention, the donor cell, whether it is introduced directly into an oocyte or used as a source of a donor nucleus or a donor metaphase plate that is introduced into an oocyte, is a quiescent cell (i.e., a cell is at G0, see, for instance, Wilmut et al., Nature, 385, 810-3 (1997); Campbell et al., WO 97/07669), a proliferating cell (Stice et al., U.S. Pat. No. 5,945,577), a metaphase cell, a cell arrested at metaphase, or a cell arrested at late G1 phase. Preferably, a donor cell is at metaphase, arrested at metaphase, or arrested at late G1 phase, more preferably arrested at metaphase or arrested at late G1 phase, most preferably arrested at late G1. Placing the metaphase donor genetic material into an oocyte is advantageous because it facilitates additional exposure to cytoplasmic reprogramming factors needed for reprogramming donor genetic material that has been introduced into the oocyte. Placing the donor genetic material arrested at late G1 into an oocyte is advantageous because the donor nucleus is prepared to undergo DNA replication during S phase of the first cell cycle of the NT embryo.

Whether a donor cell is quiescent, proliferating, at metaphase, arrested at metaphase, or arrested at late G1 phase can be determined by methods known to the art. For example, a donor cell at metaphase is a cell that has progressed through the cell cycle including the prophase stage of mitosis; the centromeres joining the condensed sister chromatids are present in the region of the equatorial plane of the cell, and the nuclear membrane is absent. The appearance of the chromosomes of a metaphase cell is known to the art and is referred to as the metaphase plate. For example, a donor cell at late G1 is a cell that has intracellular concentrations of regulatory proteins, for instance, cyclin A and cyclin E, that are higher than in cells at other cell cycle phases. A donor cell arrested at metaphase or arrested at late G1 phase is unable to proceed beyond metaphase into anaphase or S phase, respectively, and is therefore no longer proliferating. Quiescent cells are not in any of the four phases of the cell cycle (i.e., G1, S, G2, or M). Quiescent cells are typically considered as being in the G0 state so as to indicate that they would not normally progress through the cycle. The nucleus of a quiescent G0 cell is diploid. Thus, in contrast to a quiescent cell, a cell arrested at metaphase does not have a nucleus, and the DNA content is tetraploid. In contrast to a quiescent cell, a cell arrested at late G1 is prepared to undergo DNA replication but is still diploid.

Donor cells are typically arrested in metaphase by exposing the cells to at least one arresting agent. Useful arresting agents include nocodazole, demicolchin, colchicine, colcemid, paclitaxel, docetaxel, otoposide, vinblastine, vincristine, vinorelbine, monastrol, and taxol, preferably nocodazole. Preferably, the arrested state of the donor cell is reversible, i.e., the cell resumes proliferating when the arresting agent(s) is removed. The exposure of a population of donor cells to an arresting agent typically does not result in arrest of all the donor cells, thus those cells that are arrested (and therefore typically at metaphase) can be separated from those that are not arrested. Cells arrested at metaphase typically have an altered morphology that allows arrested cells to be separated. For instance, arrested cells grown on a surface and then exposed to an arresting agent have a "rounded up" appearance while proliferating cells are relatively flat.

Donor cells may be arrested at late G1 phase by exposing the cells to at least one arresting agent. Useful arresting agents include mimosine, aphidocoline, and inhibitors of CDK2 kinase, including for instance roscovitine or olomoucine (see, for instance, Alessi et al., Exp. Cell Res., 245, 8-18 (1998)). Preferably, roscovitine or olomoucine, more preferably roscovitine, are used to arrest donor cells in late G1. Preferably, the arrested state of the donor cell is reversible, i.e., the cell resumes proliferating when the arresting agent(s) is removed. The exposure of a population of donor cells to an arresting agent typically does not result in arrest of all the donor cells, thus those cells that are arrested (and therefore typically at late G1) can be separated from those that are not arrested. Alternatively, donor cells can be arrested by growing the cells in culture until the cells are confluent. Under these conditions, donor cells stop dividing and do not go beyond late G1 until the cell is placed in conditions more favorable for growth. Cells arrested at late G1 typically have an altered morphology that allows arrested cells to be separated. For instance, arrested cells are typically smaller in size than those cells that are not arrested at late G1. Preferably, donors cells arrested in late G1 having a size of about 15 µM to about 20 µM in size are selected for introduction into an oocyte.

Donor genetic material can be isolated from quiescent cells, proliferating cells, cells that are at metaphase, cells that are arrested at metaphase, or cells arrested at late G1 using methods known to the art (see, for instance, Collas and Barnes, Mol. Reprod. Dev., 38, 264-267 (1994). Typically, a donor nucleus can be isolated by removing the cell membrane, or further isolated by removing at least some of the cytoplasm that normally surrounds the donor nucleus.

Introducing Donor Genetic Material into an Oocyte

Isolated donor genetic material may be injected directly into an oocyte to produce the NT embryo (see, for instance, Collas and Barnes, Mol. Reprod. Dev., 38, 264-267 (1994); and Tao et al., Anim. Reprod. Sci., 56, 133-41 (1999)). A peizo element based micromanipulator may be used to facilitate microinjection tasks (see, for instance, Wakayama et al., Nature, 394, 369-74 (1998)). It is expected that a nuclear membrane will form around a metaphase plate that is introduced into an oocyte.

Alternatively, a single donor cell of the same species as the oocyte may be introduced by fusing the cell with the oocyte after the donor cell is placed in the perivitelline space of the oocyte (i.e., the space between an oocyte and the zona pellucida) to produce an NT unit. Such methods are known to the art (see, for instance, Stice et al., (U.S. Pat. No. 5,945,577)). A variety of electrofusion media can be used including e.g., sucrose, mannitol, sorbitol and phosphate buffered solution. Fusion can also be accomplished using Sendai virus as a fusogenic agent (Graham, Wister Inot. Symp. Monogr., 9, 19, 1969), or by using polyethylene glycol (PEG) (Susko-Parrish et al., U.S. Pat. No. 5,496,720). Fusion of the donor cell and the oocyte that make up an NT unit result in an NT embryo.

Typically, in electrofusion of porcine oocytes and donor cells, a fusion pulse ranging from about 150 V/mm to about 350 V/mm, more preferably about 250 V/mm, is used. The duration of the pulse may be about 20 µseconds. For electrofusion of bovine oocytes and donor cells, a fusion pulse of about 40 V/150 µm may be used. The duration of the pulse is about 20 μseconds. Multiple pulses can also be used successfully to induce cell fusion. The result is a one-cell NT embryo.

NT Embryo

If desired, an NT embryo can be cultured in media. The type of media can depend on the species of oocyte. For instance, for pig cells, NCSU-23 or other pig embryo culture medium (see, for instance, Tao et al., *Anim. Reprod. Sci.*, 56, 133-41 (1999)) can be used. Preferably, for pig cells, a sequential media system is used. The first medium of the sequential media system is a bicarbonate-buffered culture medium that includes alanine, alanyl-glutamine, asparagine, aspartic acid, calcium chloride, EDTA, glucose, glutamate, glycine, human serum albumin, magnesium sulphate, penicillin G, potassium chloride, proline, serine, sodium bicarbonate, sodium chloride, sodium hydrogen phosphate, sodium lactate, sodium pyruvate, and taurine is used. Such a culture medium is available under the trade designation G1.2 (Vitrolife, Inc., Englewood Colo.). The second medium of the sequential media system is a bicarbonate-buffered culture medium that includes alanine, alanyl-glutamine arginine, asparagine, aspartic acid, calcium chloride, calium pantothenate, choline chloride, cystine, folic acid, glucose, glutamate, glycine, Histidine, human serum albumin, i-inositol, isoleucine, leucine, lysine, magnesium sulphate, methionine, niacinamide, penicillin G, phenylalanine, potassium chloride, proline, pyridoxine, riboflavin, serine, sodium bicarbonate, sodium chloride, sodium Hydrogen phosphate, sodium lactate, sodium pyruvate, thiamine, threonine, tryptophan, tyrosine, valine. Such a culture medium is available under the trade designation G2.2 (Vitrolife, Inc.). This sequential media system is referred to herein as G1/G2, or G1.2/G2.2. For cow cells, G1/G2, KSOM, CR, or TCM-199, G1/G2, can be used. The NT embryo is typically incubated for up to about 10 hours. Preferably, an NT embryo is not incubated so long that the chromosomes begin to disassociate from each other, and/or micronuclei are formed after activation. Alternatively, an NT embryo need not be cultured in media.

If the oocyte used to produce the NT embryo was not enucleated, the NT embryo, whether incubated in medium or not, can optionally be enucleated. Enucleation of an NT embryo involves removal of maternal genetic material from the NT embryo, but not removal of donor genetic material. Enucleation of an NT embryo is discussed hereinbelow. Preferably, when the oocyte used to produce the NT embryo was not encleated, the method of the invention preferably includes enucleation of the NT embryo. Further, if the oocyte used to produce the NT embryo was not activated, the method preferably includes activation of the NT embryo. Activation of an NT embryo can be performed either before or after the enucleation step.

Enucleation

Oocytes may be enucleated before introduction of donor genetic material. Enucleation of oocytes may be accomplished microsurgically using a micropipette to remove the polar body and the adjacent cytoplasm, or by chemical treatment (see, for instance, Baguisi et al., *Theriol.*, 53, 290 (2000). If enucleation is performed prior to introduction of donor genetic material, it may be conducted using methods previously described for enucleating MII oocytes (Tao et al., *Anim. Reprod. Sci.*, 56, 133-41 (1999)) or by methods such as described by Goto et al., (*Anim. Sci. J.*, 70, 243-245 (1999)). The oocytes may then be screened to identify those successfully enucleated. This screening can be done by staining the oocytes with a detectable marker that specifically binds to DNA (for instance, 1 μg/ml 33342 Hoechst dye in HEPES buffered hamster embryo culture medium (HECM, Seshagine et al., *Biol. Reprod.*, 40, 544-606, (1989)), and then viewing under ultraviolet irradiation for less than 10 seconds either the oocytes or the cytoplasm and maternal genetic material removed during the enucleation procedure. The oocytes that have been successfully enucleated can then be placed in a suitable culture medium, e.g., TCM-199, G1/G2, or CR1aa plus 10% serum (Stice et al., U.S. Pat. No. 5,945, 577).

In vitro matured oocytes enucleated before introduction of donor genetic material can be enucleated when they are at the appropriate stage, e.g., immature germnal vesicle, maturing (MI to MII), or mature. In vivo matured oocytes enucleated before introduction of donor genetic material can be enucleated after isolation, preferably immediately after isolation.

If the oocyte used to produce the NT embryo was not enucleated, then the NT embryo can be enucleated. Within the NT embryo, the maternal genetic material can be distinguished from the donor genetic material by, for instance, the position of the donor nucleus within the NT embryo, formation of the first polar body, or a combination thereof. The known location of the donor genetic material within the NT embryo is based on where it was placed in the perivitelline space in relation to the location of the maternal genetic material. The maternal genetic material is near the opening placed in the zona pellucida during transfer of the donor genetic material, preferably the donor genetic material is placed away from that area. Therefore that area of cytoplasm (near the opening in the zona) can be removed via either enucleation pipette or by expulsion of cytoplasm through the opening in the zona, preferably by enucleation pipette (see, e.g., Prather et al., *Biol. Reprod.*, 37, 859 (1987); and Goto et al., *Anim. Sci. J.*, 20, 243-245 (1999)). With regard to the second method, in some cases the oocyte may progress in meiosis to MII after introduction of the donor genetic material. If so, then the first polar body can also be used as landmark to find the maternal genetic material. Hoechst dye can be used to visualize genetic material, including confirming the presence of the maternal genetic material in the removed cytoplasm. These methods may be used alone or in conjunction with each other to verify location of chromosomes and verify enucleation of the oocyte.

An NT embryo that contains both maternal and donor genetic material need not be immediately enucleated or, in some aspects of the invention, is not enucleated at all. That is, the NT embryo will at least transiently contain both maternal genetic material and donor genetic material. For instance, Willadsen et al. (*Nature*, 320, 63-65 (1986)), used non-enucleated NT embryos derived from MII oocytes to produce cloned sheep embryos. It is expected that maternal genetic material may contribute to only the placenta, thus the cells that develop to eventually form a fetus or offspring would not contain maternal genetic material.

Activation

An oocyte or an NT embryo may be activated using artificial activation methods known to the art (see, for instance, Susko-Parrish et al., (U.S. Pat. No. 5,496,720); and Stice et al., (U.S. Pat. No. 5,945,577)). An oocyte may be activated before introduction of donor genetic material, or at the same time as the introduction of donor genetic material. Alternatively and preferably, an NT embryo may be activated. Typically, when an oocyte is activated before introduction of donor genetic material, the activated oocyte is used immediately or within about 10 hours after activation. When an NT embryo is activated, activation is done at about the same time as introduction of the donor genetic material or up to about 10 hours following introduction.

Activation may include the use of agents that decrease protein phosphorylation in the cell, decrease protein synthesis by the cell, or increase the level of cations in the cell. Protein phosphorylation can be decreased by the use of agents that inhibit phosphorylation, including, for instance, a serine-threonine kinase inhibitor like 6-dimethylaminopurine, staurosporine, 2-aminopurine, or sphingosine. Protein phosphorylation can also be decreased by the use of agents that cause dephosphorylation of proteins, including for instance phosphatases A or B. Agents that decrease protein synthesis by the cell include, for instance, cycloheximide. Agents that increase the level of cations in the cell include, for instance, ionomycin, ionophores, ethanol, media free of $Mg^{++}$ and $Ca^{++}$, phorbol esters, and electrical shock. Other agents that can be used include thimerasol and DTT (Machaty et al., *Biol. Reprod.*, 57, 1123 (1997)).

Activation of porcine oocytes and NT embryos may use about 1% to about 20% ETOH, preferably 8% ETOH in KSOM or G1/G2 culture medium for 10 minutes followed by about 1 mM to about 10 mM DMAP, preferably about 2 mM DMAP in KSOM or G1/G2 for 5 hours. Preferably, porcine oocytes and NT embryos are activated by applying two pulses of from about 50 V/mm to about 200 V/mm (direct current), more preferably about 75 V/mm. The two pulses are each preferably about 60 μseconds long, and preferably separated by about a 5 second interval. Preferably, the activation is done in Zimmermann fusion media (Zimmermann et al., *Membrane Biol.*, 67, 165-182 (1982)).

Bovine oocytes and NT embryos may be activated by the method of Yang et al. (*Biol. Reprod.*, 42(Suppl 1), 117 (1992)), more preferably, by exposing bovine oocytes to about 1 μM to about 100 μM ionomycin, preferably about 50 μM ionomycin, for 10 minutes and about 1 μg/ml to about 100 μg/ml cycloheximide, preferably about 10 μg/ml cycloheximide, for about 2 hours to about 10 hours, preferably about 6 hours. Preferably, bovine oocytes and NT embryos are activated by exposure to agents that increase the level of cations in the cell, followed by exposure to agents that agents that decrease protein synthesis in the cell and/or agents that are microfilament inhibitors. Most preferably, bovine oocytes and NT embryos are exposed to about 1 μM to about 100 μM calcium ionophore, preferably about 5 μM calcium ionophore, for about 10 minutes. This is followed by incubation in about 1 μg/ml to about 10 μg/ml cytochalasin B, preferably about 5 μg/ml cytochalasin B, and about 1 μg/ml to about 100 μg/ml cycloheximide, preferably about 10 μg/ml cycloheximide, for about 1 hour. This is followed by incubation in about 1 μg/ml to about 100 μg/ml cycloheximide, preferably about 10 μg/ml cycloheximide, for about 5 hours. Preferably, after the activation treatments, bovine NT embryos are cultured in BARC medium (Powell et al., *Theriogen.*, 55, 287 (2001)).

Whether a porcine or bovine oocyte or a porcine or bovine NT embryo has been activated can be determined by observing swelling of the donor nucleus, and cleavage of the embryo about 10 hours to about 30 hours after activation.

Instead of using artificial activation methods, or in conjunction with artificial activation methods, fertilized oocyte cytoplasm can be used to activate an oocyte or an NT embryo. The use of fertilized oocyte cytoplasm to activate an oocyte or an NT embryo is referred to herein as "natural activation." Fertilized oocyte cytoplasm can be obtained by removal of cytoplasm from an oocyte that has been fertilized by a sperm. Fertilized oocyte cytoplasm can be removed by pipette and then injected directly into the oocyte or NT embryo that is to be activated. It is expected that fertilized oocyte cytoplasm can be injected in volumes up to between about 10% and about 50% the volume of the oocyte or NT embryo that is to be activated. Alternatively, instead of adding fertilized oocyte cytoplasm to the NT embryo that is to be activated, the donor genetic material present that has been introduced to an oocyte to form an NT embryo can be removed and transferred to an enucleated fertilized oocyte. Preferably, the donor genetic material is transferred from an NT embryo to an enucleated fertilized oocyte between about 2 hours and about 6 hours after the NT embryo is produced. Preferably, the fertilized oocyte into which the donor genetic material is transferred is enucleated between about 0 hours (i.e., immediately) and about 5 hours after fertilization. Preferably, the donor genetic material is transferred into the enucleated fertilized oocyte immediately after it is enucleated.

Assessment of Successful Nuclear Reprogramming and Transfer of Activated NT Embryos Successful nuclear reprogramming is evaluated by determining if activated NT embryos develop to the blastocyst stage. For both pig and cow, development of an activated NT embryo to blastocyst is typically complete in seven days, and typically includes the trophoblast and inner cell mass.

An activated NT embryo may be transferred immediately into a recipient animal or cultured for up to about 8 days in, for instance, KSOM medium, NCSU-23 medium, BARC medium, G1.2/G2.2 culture medium, or others well known to the art (see for instance Stice et al., U.S. Pat. No. 5,945,577; Wells et al., *Biol. Reprod.*, 60, 996-1005 (1999 ); and Tao et al., *Anim. Reprod. Sci.*, 56, 133-41 (1999)). Preferably, an activated NT embryo is cultured for between about 12 hours to about 36 hours (for porcine NT embryos) or for about 7 to about 8 days (for bovine NT embryos). Then, intact NT embryos (some cleaved) are transferred into a synchronous recipient animal, i.e., the transferred NT embryo is at the same stage, or about a day before or a day after, as a fertilized embryo would be in the recipient. For pigs, from about one-to about 300 NT embryos can be transferred into each recipient female but typically about 50 to about 150 embryos are transferred and ideally 100 embryos are transferred. Methods of surgical and non-surgical transfer in animals is well known in the art. For instance, surgical and non-surgical transfer in pigs is described by Curnock et al.,(*Amer. J. Vet. Res.*, 37, 97-98 (1976 )), and Hazeleger et al., (*Theriogenol.*, 51, 81-91 (1999)). Preferably, the animal is of the same species as the donor genetic material of the NT embryo.

Ultrasound and non-return to estrus is used to determine which recipients are pregnant. If needed for tissue or cell transplantation NT fetuses can be harvested during the pregnancy either surgical recovery. If live calves or pigs are desired the pregnancy lasts approximately 285 days or 114 days respectively, and some offspring may require neonatal assistance in the form of oxygen supplementation and other interventions (Hill et al., *Theriogenol.*, 51, 1451 (1999)).

The present invention is illustrated by the following examples. It is to be understood that the particular examples, materials, amounts, and procedures are to be interpreted broadly in accordance with the scope and spirit of the invention as set forth herein, and are not intended to limit the invention in any way.

EXAMPLE 1

Arrest of Donor Cells in Metaphase

Conventional nuclear transfer methods use a quiescent donor nucleus that must undergo nuclear membrane breakdown prior to reprogramming events. By starting with a metaphase donor, reprogramming of the donor genetic material is expected to be hastened by having the chromatin more accessible to reprogramming factors early on in the process.

Bovine somatic granulosa cells were obtained from granulosa harvested from the ovary. Bovine fibroblast cells were obtained from a skin biopsy at the tail and/or ear. Pig fibroblast cells were obtained from a skin biopsy of an ear. Cells were arrested in metaphase using a short reversible exposure in nocodazole at low doses (Table 3). Briefly, cells were cultured at about 30% to about 50% confluency were cultured in media (DMEM:Hams F12) containing nocodazole. After various exposures, the cells were stained with 1 µg/ml Hoechst and the number and percentage of cells in metaphase was calculated. The exposures were known to be reversible since removal of the nocodazole resulted in a decrease in the number of metaphase cells, and the cells were viable when stained with a vital dye after 24 hours incubation. In preliminary experiments, nocodazole arrest of somatic cells was also reversible (Table 3). However when higher amounts of nocodazole (10 µg) and/or longer exposure were used obvious cell death was observed in the cell cultures. The metaphase-arrested somatic cells have a rounded up morphology in culture plates. Therefore micromanipulators and glass pipettes were used to "pluck" these cells from the dishes. An 80% or greater pure population of metaphase stage cells was isolated from these dishes.

TABLE 3

Percentage of bovine somatic cells in culture arrested with various concentrations and exposures to nocodazole with 200 observed in each group.

| | Nocodazole concentration in culture medium | | | |
|---|---|---|---|---|
| Exposure | 0 ug/ml | 0.3 ug/ml | 1.0 ug/ml | 3 ug/ml |
| 3 hours | 3% | 10% | 8% | 9% |
| 10 hours | 4% | 26% | 25% | 27% |

For pig fibroblast cells, the cells (at about 50% of confluency) were cultured in the medium DMEM:F12 supplemented with 0.3 µg/ml nocodazole (Sigma, St. Louis, Mo.), a microtubule polymerization inhibitor, for 10 hours to induce M phase arrest. After gentle pipetting, cells floating in the medium were collected. Using these synchronization procedures, approximately 80% of the collected cells were arrested at M phase, and determined by flow cytometry. The metaphase cells were further purified at the time of nuclear transfer so that only cells containing a metaphase plate were used to produce M-phase derived NT embryos.

EXAMPLE 2

Arrest of Donor Cells in Late G1 Phase

The purpose of the present experiment was to examine cell cycle phases of both bovine granulosa and porcine fibroblast cells after treatment with the cell cycle inhibitors roscovitine, olomoucine, mimosine, aphidicolin, and staurosporine. Staurosporine arrests cells in early G1 phase, acting upstream of CDK2. Olomoucine and roscovitine arrest in late G1 phase, and have been shown to resume progression back to S phase with faster kinetics than staurosporine (Alessi et al., *Exp. Cell Res.*, 245, 8-18 (1998). Aphidicolin arrests at the late G1/S border (acts after phosphorylation of pRB). The cell cycle phases were examined using flow cytometry to measure cellular DNA content, which allowed for the estimation of percentages of cells in late G1, S, and G2/M phases of the cell cycle.

Experimental Design

A primary cell line was established from granulosa cells (GCs) collected by aspirating ovarian antral follicles from a 13-year old Angus beef cow of high genetic merit, using ultrasound guided transvaginal aspiration. The fibroblast cells were isolated from skin biopsies and then grown out as skin explants for one week. The collected cells were centrifuged and washed once in culture medium before seeding into a six-well tissue culture plate (Nalge Nunc International, Rochester, N.Y.). The cells were cultured in Dulbecco's Modified Eagle's medium (DMEM) F-12 (Sigma) supplemented with 10% fetal bovine serum (FBS, BioWhitaker Inc, Walkersville, Md.) and 1% (volume:volume) penicillin/streptomycin (10,000 U/ml penicillin G, 10,000 µg/ml streptomycin, Sigma) at 37.5° C. in a humidified atmosphere of 5% $CO_2$ and 95% air. After a week in culture, the cells were passaged using 0.25% trypsin-EDTA solution (Sigma) and plated into 75 $cm^2$ tissue culture flasks. When the cells were cultured to confluency, the cells at passage 2 were collected after trypsin treatment and frozen in DMEM-F12 supplemented with 40% fetal bovine serum and 10% (volume:volume) dimethyl sulfoxide (Sigma). Cells were intially frozen at −70° C. and then stored at approximately −176° C.

Frozen stocks of porcine fibroblast and bovine granulosa cells were thawed (passage 2) and cultured for 2 days. Cells were passaged 3-5 times before seeding 250,000 cells/75 $cm^2$ flask. Cells were allowed to culture for 1 day in the 75 $cm^2$ flask. Chemical inhibitors were then added to the cells to yield the appropriate final concentration, and the cells were placed in a 38° C. incubator for 26 hours. All chemical inhibitors were dissolved in DMSO as 2 mM stocks, with the exception of staurosporine, which was dissolved in methanol.

The chemical inhibitors were removed by centrifugation of the cells after trypsin treatment. Cells were resuspended in 1 ml cold PBS and fixed with 4 ml cold ethanol and placed in freezer for up to two weeks before flow cytometry. Prior to flow cytometry, cells were pelleted and resuspended in 1 ml PBS, and 1 mg/ml DNAse free RNAse was added. Cells were placed in the 38° C. incubator for 30 minutes, then 200 µg of 1 mg/ml propidium iodide, which intercalates into the DNA, was added to stain the cells. Cells were placed through a mesh filter and transferred to sample tubes for analysis by flow cytometry. Cells in different stages of the cell cycle contain varying amounts of DNA. For instance, cells in the G2/M phase contain about twice the amount of DNA (since the cell is about to divide) as the G1 phase, and the S phase will contain varying amounts between G1 and G2/M. The amount of PI fluorescence emitted is linearly related to the amount of DNA. Flow cytometry was done using a Beckman Coulter EPICS Elite Analyzer (Fullerton, Calif.) with a 488 nM laser, and 15 mW power. The software was EXPO 32 version 1.0 (Beckman Coulter). Fluorescence was collected at 635 nM band pass filter. Clumps of two or more cells were gated out by plotting peak propidium iodide fluorescence versus integral propidium iodide fluorescence. About 7,500 to about 10,00 viable cells were analyzed per sample by discriminating on propidium iodide fluorescence using the following settings: forward scatter, 260V and 7.5 gain; side scatter, 320V and 5 gain; and PMT4, 525V and 5 gain. All settings were by linear amplification (not log).

Results

TABLE 4

Bovine granulosa cells treated with roscovitine (Ros) and olomoucine (Olo). Data is expressed as a percentage of cells in each stage.

|  | Late G1 | S | G2/M |
| --- | --- | --- | --- |
| 0 Control | 71.46 | 10.25 | 18.24 |
| 0 Control | 72.65 | 10.03 | 18.27 |
| 15 μM Ros | 79.05 | 4.14 | 16.97 |
| 15 μM Ros | 79.78 | 3.90 | 16.29 |
| 30 μM Ros | 79.08 | 3.90 | 14.41 |
| 30 μM Ros | 77.85 | 4.38 | 14.42 |
| 100 μM Olo | 68.70 | 9.07 | 10.10 |
| 100 μM Olo | 67.73 | 7.58 | 8.49 |

TABLE 5

Pig ear fibroblasts treated with roscovitine and olomoucine. Data is expressed as a percentage of cells in each stage.

|  | Late G1 | S | G2/M |
| --- | --- | --- | --- |
| 0 Control | 51.81 | 21.66 | 6.72 |
| 0 Control | 55.21 | 20.90 | 21.72 |
| 15 μM Ros | 60.68 | 15.87 | 23.80 |
| 15 μM Ros | 61.63 | 15.73 | 23.37 |
| 30 μM Ros | 69.67 | 13.01 | 17.13 |
| 30 μM Ros | 68.49 | 12.85 | 17.83 |
| 100 μM Olo | 19.12 | 72.83 | 8.21 |

TABLE 6

Averaged granulosa cells (the average of the two replicates in table 4) treated with roscovitine and olomoucine. Data is expressed as a percentage of cells in each stage.

|  | Late G1 | S | G2/M |
| --- | --- | --- | --- |
| 15 μM Ros | 79.42 | 4.02 | 16.63 |
| 30 μM Ros | 78.47 | 4.14 | 14.42 |
| 100 μM Olo | 68.22 | 8.33 | 9.30 |
| Control | 72.06 | 10.14 | 18.26 |

TABLE 7

Averaged pig ear fibroblast cells (the average of the two replicates in table 5) treated with roscovitine and olomoucine. Data is expressed as a percentage of cells in each stage.

|  | Late G1 | S | G2/M |
| --- | --- | --- | --- |
| 15 μM Ros | 61.16 | 15.80 | 23.59 |
| 30 μM Ros | 69.08 | 12.93 | 17.48 |
| 100 μM Olo | 19.12 | 72.83 | 8.21 |
| Control | 53.51 | 21.28 | 14.22 |

The above studies demonstrate that roscovitine is superior to olomoucine in arresting cells in late G1. In addtition, roscovitine at 15 μM produces similar results to the higher concentration (30 μM).

In a final study, roscovitine treated, serum-starved and cycling control cells were analyzed to examine the phase of cell cycle by using flow cytometry. A group of bovine granulosa cells isolated and propagated as described above were then cultured in media with 0.5% serum for 4 days and another group of donor cells was exposed to 15 μM roscovitine for 24 hours. The roscovitine group had more cells in late G1 phase than the serum starved group and controls (82.4±0.2% vs 76.7±1.2% and 75±0.2%, respectively, p<0.05). There was not a significant difference between serum-starved cells and control cells in the late G1 phase. The percentage of cells in G2-M phase in the roscovitine group was significantly lower than serum-starved and controls (9.5±0.1% vs 13.9±0.5%, 16.5±0.1%; respectively, p<0.05).

EXAMPLE 3

Arrest of Oocytes in MI

Methods

Porcine ovaries were collected from a local slaughterhouse and transported in 0.9% saline at approximately 32° C. Follicles greater than 3 mm in diameter were aspirated with an 18-gauge needle using vacuum suction (100 mmHg; 28 ml/min). Aspirated oocytes that had an evenly granulated cytoplasm and were surrounded by at least two uniform layers of compact cumulus cells were selected and washed three times in HEPES-buffered synthetic oviductal fluid medium (Tervit et al., *J. Reprod. Fertil.*, 30, 493-497 (1972)). Oocytes were transferred into tubes containing HEPES-buffered TCM-199 (Gibco BRL, Grand Island, N.Y.) supplemented with 0.57 mM cysteine, 10 ng/ml epidermal growth factor (Sigma), 100 IU/ml penicillin, 100 μg/ml streptomycin, 0.25 ng/ml amphotericin, 0.01 IU/ml porcine FSH (Sioux Biochemicals, Sioux Center, Iowa), 0.01 IU/ml porcine LH (Sioux Biochemicals) and 0.1% (w:v) polyvinyl alcohol (in vitro maturation (IVM) medium) (Abeydeera et al., *Theriogenology*, 54, 787-797 (2000)), and shipped to the laboratory overnight at 38.5° C. Oocytes continued to be cultured in the tubes under 38.5° C. until enucleation.

In the first experiment, groups of cumulus oocyte complexes (COCs) were incubated in IVM medium at 38° C. supplemented with 1.0 or 7.5 μg/ml of cytochalasin B (Cyt B) for 5 hours (between 24 to 29 hours and 30 to 35 hours after onset of IVM, where the time of placing the cells in IVM medium was considered the onset of IVM). At the end of incubation, cumulus cells were removed from COCs by vortexing and denuded oocytes were stained with Hoechst 33342. Progress of maturation was observed under UV microscope at 29 and 35 hours after onset of IVM. Control oocytes (not exposed to Cyt B) were examined at 24, 29 and 35 hours after onset of IVM.

Results

Data from this experiment are summarized in Table 8.

TABLE 8

Proportions of pig oocytes reaching MI at 24, 29, and 35 hours after the onset of IVM

|  | 24 hours | 29 hours | 35 hours |
| --- | --- | --- | --- |
| Control | 64.4 ± 9.8% (87) | 73.0 ± 9.9%[a] (98) | 20.0 ± 3.7%[a] (94) |
| Cyt B, 1 μg/ml 24-29 hours |  | 85.6 ± 7.6%[a] (85) |  |
| Cyt B, 1 μg/ml 30-35 hours |  |  | 50.4 ± 9.7%[b] (94) |
| Cyt B, |  | 84.6 ± 6.1%[a] (88) |  |

TABLE 8-continued

Proportions of pig oocytes reaching MI at 24,
29, and 35 hours after the onset of IVM

| | 24 hours | 29 hours | 35 hours |
|---|---|---|---|
| 7.5 µg/ml 24-29 hours Cyt B, 7.5 µg/ml 30-35 hours | | | 59.0 ± 2.4%[b] (92) |

Different superscripts within column indicate significant difference, p < 0.05.
Number of oocytes examined in parentheses.

Conclusion: When examined at 29 hours after IVM, the majority of oocytes reached the M I phase. Treatment with Cyt B did not significantly increase proportion of oocytes at M I phase in comparison to control oocytes at 29 hours after IVM. At 35 hours post IVM only about 20% of control oocytes remained at M I phase. Treatment with Cyt B between 30 and 35 hours after IVM was not effective in arresting oocytes at M I phase. Therefore, in subsequent experiments, oocytes at 29 hours after IVM were used as M I oocytes.

EXAMPLE 4

Fusion of Metaphase (M) and Late G1 Arrested Porcine Fibroblasts into Enucleated M I and M II Porcine Oocytes Methods The experiment was conducted in 2×2 factorial design in which the effects of donor cell stage (M and late G1) and oocyte stage (M I vs. M II) on reconstruction of donor chromatin after fusion and activation were examined. The experimental protocol is represented in the following diagram[a]:

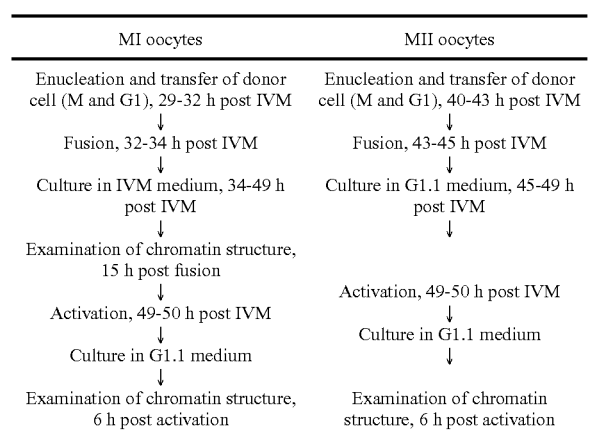

[a] "h post IVM," hours after onset of IVM; "h post fusion," hours after fusion; "h post activation," hours after activation.

Preparation of Donor Cells

Porcine fibroblasts were harvested from an ear skin biopsy obtained from an adult pig. The tissue was finely minced and digested in 0.125% (w/v) trypsin/0.02% (w/v) EDTA solution (Sigma Chemical CO., St. Louis, Mo.) containing 1 mg/ml collagenase (Sigma) and 0.3 mg/ml hyaluronidase (Sigma) for 2 h at 37° C. After digestion, the mixture was filtered through four layers of sterile gauze and cells were pelleted by centrifugation. Cells were cultured in DMEM/F-12 medium (Sigma) supplemented with 20% (v/v) FCS (Biowhittaker Inc., Walkersville, Md.) under 5% $CO_2$ in air at 37° C. After reaching confluence, cells were passaged. Passage 2 fibroblasts were trypsinized, suspended in the culture medium with 10% (v/v) dimethyl sulfoxide (Sigma) and stored as frozen aliquots. Donor cells were used for nuclear transfer between passages 3 and 9 of culture.

For preparation of donors in late G1 phase, the cells were allowed to grow to confluency and a single cell suspension was prepared by standard trypsinization. The onset of confluency resulted in the arrest of the donor cells in late G1. For preparation of donors in M phase, after 2-4 days of subculturing, the cells (which were at about 50% of confluency) were cultured in the medium supplemented with 0.3 µg/ml nocodazole (Sigma), a microtubule polymerization inhibitor, for 10 hours to induce M phase arrest. After gentle pipetting, cells floating in the medium were collected. Using these synchronization procedures, approximately 90 and 80% of the collected cells were arrested at late G1 and M phases, respectively, as determined by flow cytometry as described in Example 2. Both types of donor cells were prepared immediately prior to nuclear transfer.

Oocytes

Ovaries were collected and incubated to about 29 hours to about 32 hours without cytochalasin B as described in example 3.

Nuclear Transfer

Reconstructed embryos were produced using a modification of the method described by Miyoshi et al. (*Cloning*, 2, 175-184 (2000)). Cumulus cells were removed by vortexing with 0.1% (weight:volume) hyaluronidase and denuded oocytes were transferred into 100 µl of HEPES-buffered TCM-199 supplemented with 7.5 µg/ml cytochalasin B (Sigma) and 10% FCS with the osmolarity adjusted to 300 mOsm by adding sorbitol (manipulation medium). The M I plate or the first polar body and M II plate were removed by aspiration with a 15-µm inner diameter glass pipette. The oocytes had been previously stained in the manipulation medium supplemented with 5 µg/ml Hoechst 33342 (Sigma) for 20 minutes and confirmation of successful enucleation was achieved by visualizing the oocyte and removed cytoplasm under ultraviolet light. After enucleation, a donor cell was inserted into the perivitelline space of each enucleated oocyte using the same glass pipette. Cell-oocyte complexes were washed in TCM-199 supplemented with 10% FCS, transferred to the same medium and kept under 5% $CO_2$ in air at 38.5° C. until fusion.

Fusion was performed in a 100 mm dish filled with 15 ml of Zimmermann fusion medium (Zimmermann et al., *Membrane Biol.*, 67, 165-182 (1982)). Two stainless steel wires (100 µm diameter) attached to micromanipulators were used as electrodes. The single cell-oocyte complex was sandwiched between the electrodes and oriented with the contact surface between the enucleated oocyte and the donor cell perpendicular to the electrodes. The distance between the electrodes was about 100 µm. Membrane fusion was induced by applying a single direct current pulse of 250 V/mm for a duration of 20 µseconds with a prepulse of alternating current field of 5 V, 1 MHz for 2 seconds using an LF 101 Fusion Machine (TR Tech Co., Tokyo, Japan). Following the fusion, the NT embryos were washed in G1.2 medium (Vitrolife, Inc., Englewood Colo.) (Gandhi et al., *Mol. Reprod. Dev.*, 58, 269-275 (2001)) and cultured for a period of 1 hour in 100 μl of the same medium. Fusion was then determined by microscopic examination.

Between fusion and activation, NT embryos constructed using MI oocytes and late G1 donor cells were maintained in IVM media supplemented with Cytochalasin B. NT embryos were activated in Zimmermann's medium by applying two 60 μ second pulses of 75V DC in 5 second intervals. After activation, NT embryos were cultured for 6 hours in G1.2 medium. NT embryos reconstructed with late G1 cells were cultured for the first 2 hours in G1.2 supplemented with CytB at 7.5 μg/ml. Chromatin configuration was observed under UV microscope after staining of reconstructed embryos with 5 μg/ml Hoechst 33342 for 20 minutes. The following categories of chromatin configuration were observed: condensed chromatin (cc), swollen nucleus (sn), cc+polar body (pb), and sn+pb (cc/sn+pb).

Data were transformed by arcsin square root and analysed by one-way (data recorded before activation) or two-way (data recorded after activation) ANOVA (SigmaStat, Jandel Scientific, San Rafael, Calif.). Differences between experimental groups were analyzed by the Student-Newman-Keuls method.

Results

Patterns of chromatin configuration in oocytes reconstructed by transferring late G1 and M-phase arrested fibroblasts into M I enucleated oocytes examined before activation (about 15 hours after fusion) are summarized in Table 9.

densed stage than NT embryos reconstructed with M-phase fibroblasts. However, this difference reflects also the fact that in many M-phase reconstructed NT embryos, no chromatin was present upon examination. Interestingly, some M-phase reconstructed NT embryos were able to extrude the polar body. After activation, decondensation of the chromatin was observed in all categories of reconstructed embryos. There was significant effect of stage of recipient enucleated oocyte and stage of donor cell as well as a significant interaction between those main factors on proportion of embryos with decondensed chromatin. Decondensed chromatin was observed in significantly higher proportion of embryos reconstructed with M II enucleated oocytes and G1 cells. As expected, in some embryos reconstructed with M-phase fibroblast condensed or swollen chromatin with extruded polar body was observed.

EXAMPLE 5

Determination of Embryonic Developmental Rates of Metaphase Nuclear Transfer embryos Developed in Example 4

Methods

NT embryos were produced by using the same protocol as in Example 4. Embryos were cultured in humidified atmosphere of 5% $CO_2$ in air at 39° C. in G1.2 medium for the first 72 hours and then transferred into G2.2 medium (Vitrolife,

TABLE 9

| Donor | # of trials | # of NTs | Fusion rate (%) | # of NTs examined | cc (%) | sn (%) | cc/sn + pb (%) |
|---|---|---|---|---|---|---|---|
| G1 | 3 | 128 | $65.8 \pm 9.3^a$ | 40 | $85.4 \pm 3.5^a$ | $5.4 \pm 2.9$ | $0.0 \pm 0.0$ |
| M | 4 | 248 | $26.0 \pm 5.8^b$ | 30 | $54.9 \pm 6.8^b$ | $8.3 \pm 8.3$ | $9.0 \pm 5.9$ |

Values with different superscripts within column are significantly different, $p < 0.05$.

The following table summarizes pattern chromatin configuration examined 6 hours after activation in embryos reconstructed by transferring late G1 and M-phase fibroblasts into M I and M II enucleated oocytes.

Inc., Englewood Colo.) and cultured for additional 96 hours. Cleavage and blastocyst developmental rates were assessed after 48 and 168 hours of culture, respectively. At the end of the culture period, blastocysts were fixed and stained in order

TABLE 10

| Ooctye | Donor | # of trials | # of NTs | Fusion rate (%) | # of NTs examined | cc (%) | sn (%) | cc/sn + pb (%) |
|---|---|---|---|---|---|---|---|---|
| M I | late G1 | 3 | 128 | $65.7 \pm 3.4^a$ | 36 | $33.3 \pm 3.9$ | $53.7 \pm 4.0^a$ | $0.0 \pm 4.8$ |
|  | M | 3 | 200 | $30.4 \pm 3.4^b$ | 32 | $32.9 \pm 3.9$ | $25.1 \pm 4.0^a$ | $6.1 \pm 4.8$ |
| M II | late G1 | 3 | 75 | $62.9 \pm 3.4^a$ | 45 | $7.7 \pm 3.9$ | $90.6 \pm 4.0^b$ | $0.0 \pm 4.8$ |
|  | M | 3 | 122 | $37.4 \pm 3.4^b$ | 48 | $30.1 \pm 3.9$ | $30.5 \pm 4.0^a$ | $23.3 \pm 4.8$ |

Values with different superscripts within column are significantly different, $p < 0.05$.

Conclusions

Fusion rate was significantly higher when late G1 fibroblasts were used as a donor cell. The stage of recipient enucleated oocyte (M I or M II) did not have significant effect on fusion rate. Generally, fibroblasts arrested at M-phase appeared to be more fragile than G1 cells, and considerably more M-phase donor cells were destroyed during fusion and activation. This is reflected also in the fact that some embryos reconstructed with M-phase cells did not have any visible chromatin when examined for chromatin configuration. Before activation, significantly more NT embryos reconstructed with late G1 cells maintained chromatin at the conto examine their cell number. In the preliminary experiment, developmental ability of parthenogenetic porcine embryos, i.e., activated unfertilized embryos, in NCSU-23 vs. G1.2 culture media followed by G2.2 culture media (G1.2/G2.2 culture media) was compared. Oocytes and/or NT embryos were activated using the same method as for reconstructed NT embryos and then cultured in the two different media. Other culture parameters and assessment of development were same as applied for NT embryos. Data from preliminary culture experiments were analyzed by one-way ANOVA after arcsin square root transformation. The effects of stage of oocyte and stage of donor cell on in vitro development of NT embryos were examined by two-way ANOVA. Differences among experimental groups were tested by Student-Newman-Keuls method (SigmaStat, Jandel Scientific).

Results

Development of parthenogenetic embryos cultured in NCSU-23 and G1.2/G2.2 media is presented in Table 11.

TABLE 11

| Medium | # of trials | # of oocytes | Cleavage (%) | Blastocyst (%) | Blastocyst cell # |
|---|---|---|---|---|---|
| NCSU-23 | 5 | 179 | 33.4 ± 3.3$^a$ | 5.9 ± 1.4$^a$ | 30.0 ± 4.4 |
| G1.2/G2.2 | 5 | 240 | 53.8 ± 2.2$^b$ | 14.7 ± 2.2$^b$ | 46.0 ± 4.1 |

Values with different superscripts within columns are significantly different, $p < 0.05$.

Developmental data of NT embryos reconstructed by transferring late G1 and M-phase arrested fibroblasts into M I or M II stage oocyte are summarized in Table 12.

TABLE 12

| Oocyte | Donor | # of trials | # of NTs | Cleavage (%) | Blastocyst (%) | Blastocyst cell # |
|---|---|---|---|---|---|---|
| M I | late G1 | 4 | 180 | 5.5 ± 3.6$^a$ | 0.4 ± 0.4$^a$ | 19.0 ± 5.0 |
|  | M | 4 | 179 | 10.6 ± 3.6$^a$ | 0.0 ± 0.4$^a$ |  |
| M II | late G1 | 3 | 227 | 35.3 ± 4.2$^b$ | 7.6 ± 0.5$^b$ | 45.1 ± 6.2 |
|  | M | 3 | 136 | 17.9 ± 4.2$^{ab}$ | 0.0 ± 0.5$^a$ |  |

Values with different superscripts within columns are significantly different, $p < 0.05$.

Conclusions

Preliminary experiments have shown that significantly better cleavage rate and blastocyst development was achieved when embryos were cultured in G1.2/G2.2. Thus, this sequential media system was selected for culture of NT embryos. Cleavage ratio of NT embryos reconstructed from M II enucleated oocytes was significantly higher than cleavage of embryos reconstructed from M I enucleated oocytes. The stage of donor cell did not affect cleavage rate. There was statistically significant interaction between stage of enucleated oocyte and stage of donor cell. NT embryos reconstructed with M II enucleated oocytes and late G1 fibroblasts cleaved at a significantly higher rate than embryos reconstructed from M I enucleated oocytes. Similar correlations have been found analyzing proportion of blastocyst development. In this case, stage of the donor cell also had significant effect on blastocyst development, that is, NT embryos reconstructed with late G1 cells developed to the blastocyst stage at a higher proportion than NT embryos reconstructed with M-phase fibroblasts. In fact, it was possible to produce blastocyst reconstructed using M I enucleated oocyte and late G1 fibroblast. This proves that M I enucleated oocytes have the ability to support embryo development after nuclear transfer; however, the development was lower in comparison to M II enucleated oocytes.

These data indicate that M I porcine enucleated oocytes have the capability to reprogram the donor nucleus as evidenced by chromatin decondensation and extrusion of polar bodies. Also, embryos reconstructed from M I oocytes and late G1 fibroblasts can develop to the blastocyst stage after in vitro culture. Although the development of NT embryos reconstructed from M II enucleated oocytes was significantly better than of embryos reconstructed from M I enucleated oocytes, the evidence indicates that M I enucleated oocytes can be used for production of porcine NT embryos. In addition, the further use of M I enucleated oocytes in cloning can serve as valuable experimental tool to study reprogramming events after nuclear transfer. These findings provide a foundation for future studies in which the NT embryos are transferred into recipient animals.

When transferred into recipient animals, the NT embryos are cultured for between about 12 hours to about 36 hours and then intact NT embryos (some cleaved) are transferred into a synchronous recipient gilt or sow. One to 300 NT embryos can be transferred into each recipient female but typically about 50 to about 150 embryos are transferred and ideally about 100 embryos are transferred. Methods of surgical and non-surgical transfer in pigs are well known in the art (Hazeleger et al., (*Theriogenol.*, 51, 81-91 (1999)). Ultrasound and non-return to estrus are used to determine which recipients are pregnant. NT fetuses if needed for tissue or cell transplantation can be harvested during the pregnancy through surgical recovery. If live pigs are desired the pregnancy last approximately 114 days and some pigs may require neonatal assistance in the form or oxygen supplementation and other interventions (Hill et al., *Theriogenol.*, 51, 1451 (1999)).

EXAMPLE 6

Exposure of NT Embryos to Fertilized Cytoplasm

Porcine NT embryos are produced as described in Example 4. In vitro derived porcine oocytes are isolated as described in Example 3 and allowed to mature for 42 hours. Alternatively, in vivo derived porcine oocytes are isolated using methods known to the art. Porcine sperm is isolated using methods known to the art. Mature oocytes are fertilized by exposure to sperm, and incubated for about 2 hours in NCSU-23 media before cytoplasm is removed or before enucleation (i.e., removal of the maternal genetic material and the genetic material donated by the sperm). Cytoplasm is removed from fertilized oocytes by using a micropipette.

NT embryos are activated using a combination of artificial activation and natural activation, or by natural activation alone. Briefly, NT embryos are incubated for 2 hours in NCSU-23 media after fusion. The NT embryos that are artificially activated are so activated by exposure to ionomycin and DMAP of other suitable activation agents. Activated NT embryos are incubated for an additional 0 to 5 hours before fertilized cytoplasm is injected or fused into the cytoplasm of the NT embryos.

The same methods of adding fertilized cytoplasm are used for both artificially activated NT embryos and NT embryos that have not been artificially activated. A volume of fertilized cytoplasm equivalent to about 10% or about 50% of the NT embryo is injected into the NT embryo. The NT embryos are then incubated as described in Example 5. In another method of exposing the donor genetic material of an NT embryo to fertilized oocyte cytoplasm, the donor genetic material is removed from the NT embryo about 2 to 6 hours after introduction of the donor genetic material. The removed donor genetic material is transferred to a fertilized oocyte that has been enucleated.

EXAMPLE 7

Cattle Cloning Using an MI Oocyte

Isolation of Granulosa Cells

A primary cell line was established from granulosa cells (GCs) collected by aspirating ovarian antral follicles from a 13-year old Angus beef cow of high genetic merit, using ultrasound guided transvaginal aspiration. The collected cells were centrifuged and washed once in Dulbecco's Modified Eagle's medium (DMEM) F-12 (Sigma, Louis, Mo.) supplemented with 10% fetal bovine serum (FBS, Bio Whitaker Inc, Walkersville, Md.) and 1% (volume:volume) penicillin/streptomycin (10,000 Units/ml penicillin G, 10,000 µg/ml streptomycin, Sigma) before seeding $10^6$ to $10^7$ cells into a six-well tissue culture plate (Nalge Nunc International, Rochester, N.Y.). The cells were cultured in the culture medium at 37.5° C. in a humidified atmosphere of 5% $CO_2$ and 95% air. After a week in culture, the cells were passaged using 0.25% trypsin-EDTA solution (Sigma) and about $10^6$ cells plated into 75 cm$^2$ tissue culture flasks. When the cells were cultured to confluency, the cells at passage 2 were collected after trypsin treatment and frozen in DMEM-F12 supplemented with 40% fetal bovine serum and 10% (volume:volume) dimethyl sulfoxide (Sigma).

Donor Cell Preparation and Transfer

Granulosa cells frozen at passage 2 were thawed and recultured in a six-well tissue culture plate for 4 days in DMEM F-12 containing 10% FCS. When the cells were cultured to 80% of confluency in each well, cells from one well of a six-well plate were dissociated by trypsinization with 0.25% trypsin-EDTA solution (Sigma) and half of the cells were plated into one 35 mm plate. After 24 hours of culture at 37.5° C. in a humidified atmosphere of 5% $CO_2$ and 95% air, the DMEM F-12 containing 10% FCS medium was changed to the same culture medium containing 15 µM roscovitine (Sigma) and the cells were cultured in this medium for an additional 24 hours. After 24 hours of roscovitine treatment, the cells were pelleted and resuspended in DMEM F-12+ 10% FBS containing 15 µM roscovitine and further incubated in this medium at 39° C. in 5% $CO_2$ until nuclear transfer. Granulosa cells at the same passage number were cultured for four days in DMEM F-12 medium containing 0.5% FBS after three days of culture with 10% FBS. On the day of nuclear transfer, granulosa cells were trypsinized, pelleted and resuspended in DMEM/F-12 medium containing 0.5% FBS prior to transfer into enucleated oocytes. A single cell was inserted into the perivitelline space of the enucleated oocyte by using a 15 µm (internal diameter) glass pipette. For the roscovitine treatment, oocyte enucleation and nuclear transfers were performed in TL-HEPES (Bio Whittaker, Walkersville, Md.) containing 15 µM roscovitine. Oocyte-cell complexes were placed in TCM 199 (Gibco Inc, Grand Island, N.Y.) containing 10% FCS and 15 µM roscovitine at 39° C. in 5% $CO_2$ in air until fusion. When serum-starved cells were used, the procedures were the same but the medium did not contain roscovitine.

Oocyte Preparation

In vitro maturation of bovine immature oocytes and enucleation were performed as described previously (Cibelli et al., *Science*, 280, 1256 (1998); Wells et al., *Biol. Reprod.*, 60, 996-1005 (1999); and Kubota et al., *Proc. Natl. Acad. Sci. USA*, 90, 990-995 (2000)). Briefly, bovine cumulus-oocyte complexes (COCs) were recovered by aspiration of small antral follicles on ovaries obtained from a slaughterhouse. Only COCs with a compact, nonatretic cumulus oophorus-corona radiata and a homogenous ooplasm were selected. They were matured in TCM 199 (Gibco Inc, Grand Island, N.Y.) supplemented with 10% FBS, 50 µg/ml sodium pyruvate, 1% (volume:volume) penicillin/streptomycin (10,000 Units/ml penicillin G, 10,000 µg/ml streptomycin), 1 ng/ml rIGF-1 (Sigma), 0.01 Units/ml bLH and 0.01 Units/ml bFSH (Sioux Biochem. Sioux Center, Iowa) in four-well plates overlaid with mineral oil. Maturation was performed at 39° C. in a humidified 5% $CO_2$ in air for 16-18 hours. After maturation, the cumulus-corona was totally removed by vortexing COCs in TL HEPES medium containing 100 Units/ml hyaluronidase (Sigma). Oocytes matured for 16-18 hours were enucleated in MII phase with a 15 µm (internal diameter) glass pipette (Ependorf Munich, Germany) by aspirating the first polar body and MII plate in a small volume of surrounding cytoplasm in TL HEPES supplemented with 7.5 µg/ml Cytochalasin B (Sigma). The oocytes were previously stained in TL HEPES containing 2 µg/ml Hoechst 33342 and 7.5 µg/ml Cytochalasin B for 10-15 minutes. Enucleation was performed under ultraviolet light to ensure removal of oocyte chromatin.

Fusion, Activation, and Culture of NT Units

Oocyte-granulosa NT units were fused by using a needle-type electrode (Miyoshi et al., *Biol. Reprod.*, 62, 1640-1646 (2000); Goto et al., *Anim. Sci. J.*, 70, 243-245 (1999)) in Zimmermann's fusion medium (Zimmermann et al., *Membrane Biol.*, 67, 165-182 (1982)). The single cell-oocyte NT unit was sandwiched between two wires arranged in a straight line and attached to micromanipulators. The contact surface between the oocyte and the donor cell was parallel to the electrodes. The distance between the electrodes was approximately 150 µm (the diameter of the oocytes). A single direct current pulse of 40 V for a duration of 20 µseconds was applied. Following the pulse, the complexes were cultured in TCM 199 supplemented with 10% FBS for 2 hours and fusion rates were determined.

Activation of NT embryos was performed as described previously (Goto et al., *Anim. Sci. J.*, 70, 243-245 (1999); Lui et al., *Mol. Reprod Dev*, 56, 145-148 (1998)) after modification. Briefly, 2 hours after fusion, NT embryos were exposed to 5 µM calcium ionophore (free acid, Sigma) for 10 minutes, followed by incubation in TCM 199 supplemented with 10% FBS, 5 µg/ml Cytochalasin B (Sigma), and 10 µg/ml Cycloheximide (Sigma) for 1 hour at 39° C. in 5% $CO_2$ in air and in TCM 199 supplemented with 10% FBS and 10 µg/ml Cycloheximide for 5 hrs at 39° C. in 5% $CO_2$, 5% $O_2$ and 90% $N_2$. After the activation treatments, NT embryos were cultured in BARC medium (Powell et al., *Theriogen.*, 55, 287 (2001)) in four-well plates overlaid with mineral oil at 39° C. in 5% $CO_2$, 5% $O_2$ and 90% $N_2$ for 7-8 days.

In Vitro Development

Cleavage and blastocyst formation rates were similar between NT embryos derived from roscovitine (ros) treated or serum starved (ss) cells (cleavage: 54.3±1.8% vs 57.7±5.0%, blastocysts: 12.9±0.5% vs 20.1±4.7%; respectively) at day seven.

Embryo Transfer and Birth of Calves

On day seven or eight the NT embryos were nonsurgically transferred into a synchronous recipient female (plus or minus 1 day of heat from day of fusion). Recipient animals were checked for pregnancy rates from day 35 to birth every week. Following embryo transfer, there was not significant difference in fetal developmental rate to 30-70 days (ss: 23.6±0.4%, ros: 27.8±2.7%; respectively) or to 190 days (ss: 8.4±5.9%, ros:12.5±2.0%; respectively) between transferred blastocysts derived from serum starved or roscovitine treated cells, however; the development rate beyond 200 days in the roscovitine group (12.5±2.0%) was significantly higher than the serum-starved group (3.4±1.7%, p<0.05). Two living genetically identical calves were born derived from NT embryos produced using roscovitine arrested donor cells.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method of producing a cloned non-human, non-primate mammalian NT embryo, the method comprising (a) introducing metaphase donor genetic material, in the form of a cell or nucleus, from a differentiated cell of a non-human, non-primate species into an metaphase oocyte of the same species, and (b) activating the oocyte, thereby yielding a cloned non-human, non-primate mammalian NT embryo, wherein activating comprises introducing to the oocyte cytoplasm from a fertilized oocyte.

2. A method of producing a cloned non-human, non-primate mammalian NT embryo, the method comprising (a) introducing metaphase donor genetic material, in the form of a cell or nucleus, from a differentiated cell of a non-human, non-primate species into an metaphase oocyte of the same species, and (b) enucleating the oocyte after introducing the donor genetic material to the oocyte, wherein enucleating the oocyte comprises removal of maternal genetic material and activating the oocyte, thereby yielding a cloned non-human, non-primate mammalian NT embryo.

3. A method of producing a cloned non-human, non-primate mammalian NT embryo, the method comprising (a) introducing metaphase donor genetic material, in the form of a cell or nucleus, from a differentiated cell of a non-human, non-primate species into an metaphase oocyte of the same species, wherein the oocyte is arrested at metaphase I as a result of exposure to an arresting agent, and (b) activating the oocyte, thereby yielding a cloned non-human, non-primate mammalian NT embryo.

4. The method of claim 3 wherein the oocyte is enucleated while in metaphase I.

* * * * *